United States Patent [19]

Burke et al.

[11] 4,346,037

[45] Aug. 24, 1982

[54] BASE CATALYZED ACYLATION WITH ENOL ESTERS

[75] Inventors: Howard J. Burke; Edward J. Hessler, both of Kalamazoo, Mich.

[73] Assignee: The Upjohn Company, Kalamazoo, Mich.

[21] Appl. No.: 282,314

[22] Filed: Jul. 10, 1981

[51] Int. Cl.$^3$ ............................................. C07J 71/00
[52] U.S. Cl. ......................... 260/239.55 R; 260/397.4; 260/397.45
[58] Field of Search .................. 260/239.55 R, 397.45, 260/397.4

[56] References Cited

U.S. PATENT DOCUMENTS

| | | | |
|---|---|---|---|
| 2,422,016 | 6/1974 | Hull et al. | 560/130 |
| 2,482,066 | 9/1949 | Hull et al. | 560/174 |
| 2,867,638 | 1/1959 | Lincoln et al. | 260/397.45 |
| 2,891,079 | 1/1959 | Dodson et al. | 260/397.4 |
| 3,000,914 | 9/1961 | Miramontes et al. | 260/397.4 |
| 3,043,832 | 7/1962 | de Ruggieri et al. | 260/239.55 R |
| 3,061,616 | 10/1962 | Camerino et al. | 260/397.4 |
| 3,084,174 | 4/1963 | Patchett et al. | 260/397.4 |
| 3,105,840 | 10/1963 | Beyler | 260/397.4 |
| 3,117,966 | 1/1964 | Petrow | 260/239.55 D |
| 3,147,290 | 9/1964 | Spero | 260/397.47 |
| 3,356,573 | 12/1967 | Kirk et al. | 424/243 |
| 3,400,137 | 9/1968 | Cross | 260/397.4 |

FOREIGN PATENT DOCUMENTS

| | | | |
|---|---|---|---|
| 868303 | 5/1961 | United Kingdom | 260/397.45 |
| 870286 | 6/1961 | United Kingdom | 260/397.45 |
| 886619 | 1/1962 | United Kingdom | . |

OTHER PUBLICATIONS

Kirk-Othmer *Encyclopedia of Chemical Technology*, 3rd Ed., vol. 9, John Wiley and Sons, NY, 1980, pp. 321-327.

Hagemeyer, Jr., et al., "Reactions of Isopropenyl Acetate", Ind. Eng. Chem., vol. 41, No. 12, pp. 2920-2924, (1949).

Hagemeyer, Jr. et al., *loc. cit.*, Smith and Chen. J. Org. Chem. 30., 3095-3099, (1965).

Jeffrey, et al., reports in "Part VII The Kinetics and Mechanism of the Enol-Acetylation of Acetophenone by Isopropenyl Acetate Catalysed by Toluene-p-sulphonic Acid", J. Chem. Soc. 1961.

March, *Advanced Organic Chemistry: Reactions, Mechanisms and Structure*, 1968, McGraw-Hill Book Company, p. 323.

"Steroid Reactions", by Djerassi, (1963) Holden-Day Inc., San Francisco.

*Primary Examiner*—Elbert L. Roberts
*Attorney, Agent, or Firm*—Joan Thierstein

[57] ABSTRACT

This invention relates to processes for base catalyzed acylations using enol esters, for example, isopropenyl acetate. Particularly, the processes are useful for acylating acid sensitive alcohols including hydroxy steroids.

16 Claims, No Drawings

BASE CATALYZED ACYLATION WITH ENOL ESTERS

SUMMARY OF THE INVENTION

This invention relates to processes for base catalyzed acylations using enol esters, for example, isopropenyl acetate. Particularly, the processes are useful for preparing acylated steroid compounds.

BACKGROUND OF THE INVENTION

It is well known that ester groups have a wide range of utilities. (See Kirk-Othmer *Encyclopedia of Chemical Technology*, 3rd. Ed. Vol. 9, John Wiley and Sons, NY, 1980, pp. 321–327.) Especially valuable are pharmaceutical esters (Ibid, "Medicinals" p. 327.) Further, a large number of acylated steroids have valuable therapeutic properties, and many possess, for example, antiinflammatory, anti-neoplastic, contraceptive or estrus regulatory properties.

There are various known processes for preparing acyl esters. More specifically, isopropenyl acetate is itself generally disclosed with acid catalysts in the preparation of acetate esters. See, for example, Hagemeyer, Jr., et al., "Reactions of Isopropenyl Acetate", Ind. Eng. Chem. Vol. 41, No. 12, pp. 2920–4 (1949) and U.S. Pat. No. 2,422,016 issued to Hull, et al. Additionally, Jeffrey, et al. reports in "Part VII The Kinetics and Mechanism of the Enol-Acetylation of Acetophenone by Isopropenyl Acetate Catalyzed by Toluene-p-sulphonic Acid." J. Chem. Soc. 1961, 1906 that the reaction is catalyzed by strong acids. This reference is cited by March, *Advanced Organic Chemistry: Reactions, Mechanisms and Structure*, 1968, McGraw-Hill Book Company p. 323 to generally support a disclosure of the ease with which enol esters undergo reaction with free alcohol.

A related reference is U.S. Pat. No. 2,482,066, to a method of acetylating keto-compounds and malonic acid esters using isopropenyl acetate and a catalyst which is limited to an acid or a tertiary nitrogenous material. The tertiary amines disclosed specifically in that patent do not act as catalysts in the present invention.

DETAILED DESCRIPTION OF THE INVENTION

We have now found that an enol ester, for example, isopropenyl acetate, reacts with alcohols to prepare acyl esters or particularly acetyl esters thereof with the use of strong bases as catalysts. Such use of bases is heretofore unknown and provides simple acylation processes having high yields. The processes are particularly advantageous for acylating tertiary alcohols and, more particularly, hindered alcohols or an alcohol group or groups in compounds having one or more acid sensitive functionalities; such as enol ethers, enol esters, easily eliminated hydroxyl groups, acetals, or ketals additionally present.

Thus according to the invention there is provided a process for the preparation of a compound of formula I $$\text{ROAc} \quad \quad \text{I}$$

in which R is alkyl, alkenyl, aryl, aralkyl, cycloalkyl, alkyl substituted cycloalkyl, cycloalkenyl, heterocyclic ring or steroidal ring system; Ac is an acyl group of from 2 to 6 carbon atoms, inclusive; which comprises reacting an enol ester with an alcohol of formula II $$\text{ROH} \quad \quad \text{II}$$

wherein R is as defined above in the presence of a strong base.

The alkyl, for example, is methyl, ethyl, propyl, isopropyl, butyl, isobutyl, sec-butyl, tertiary butyl, pentyl, isopentyl, tertiary pentyl, neopentyl, branched hexyl, or heptyl; aryl, for example, is phenyl; the aralkyl, for example, is a phenyl group having at least one alkyl substituent as defined above to which the OH is attached; the alkenyl, for example, is allyl; the cycloalkyl, for example, is of from three to seven carbon atoms; the alkyl substituted cycloalkyl, for example, is methylcyclohexyl; the heterocyclic ring is, for example, a ring of 2 to 6 carbons having at least one additional atom such as oxygen, nitrogen or sulfur which is prepared in a known manner such that an —OH is attached which possesses substantially the same properties as the OH of ROH, wherein R is alkyl, including substituted and unsubstituted pyridyl, piperidyl, furyl, morpholino, thiomorpholino, pyrrolinyl, pyrrolidinyl, pyrrolyl, or thienyl, and finally the steroidal ring system, for example, is one having an OH attached at one or more of the 11, 17, and 21 positions according to numbering as shown in the skeletal structure formula Ia or Ib.

Compounds in which the OH possesses substantially the same properties as the unsubstituted alkyl, aryl, aralkyl, alkenyl, cycloalkyl, alkyl substituted cycloalkyl, cycloalkenyl, and heterocyclic compounds defined above are those wherein the R group bears one, two or more simple substituents, including but not limited to alkyl, e.g., methyl, ethyl; alkylthio, for example, methylthio; halo, e.g., chloro, bromo, cyano, nitro, sulfate, sulfonyloxy, carboxyl; carbo-lower alkoxy, e.g. carbomethoxy, carbethoxy; aralkoxy, for example, benzyloxy; alkenyloxy, for example, allyloxy; amino; mono- and di-lower alkylamino, e.g. methylamino, dimethylamino, methylethylamino; amido; arylamino; N-alkyl-N-arylamino; epoxy; lower-alkoxy, e.g. methoxy, ethoxy; lower alkanoyloxy, e.g. acetoxy, carbonyl; cycloalkoxy, for example, cyclohexyloxy; cycloalkenoxy; aryloxy, for example, substituted or unsubstituted phenoxy; arylthio; arylcarbonyl; for example, benzoyl, and additionally one, two or more hydroxy groups in the R substituent which may also be subject to acylation in the invention process. It is recognized that unsubstituted or monosubstituted amino substituents on the R group may also be subject to acylation during the invention process.

The compounds wherein R is a steroidal ring system; for which formula Ia or Ib shows the basic numbered structure comprises the preferred class of compounds of the present invention described above. This class of compounds is well known and, for example, includes cortical steroids, progestagens, androgens and estrogens. Members of each of these classes having an OH are known to exist. The OH is generally found in the α- or β-11, α- or β-17, or the 21 position of the formula Ia and Ib, respectively. The OH of each of these compounds possesses substantially the same properties as that previously defined by formula II ROH for the acylation of this invention.

More particularly the preferred steroids of formula II ROH for use in the novel processes of the present invention are selected from the compounds of:

Formula A wherein ~ is α or β; ═ is an optional double bond; $R_2$ is hydrogen or halo wherein halo is fluoro, chloro, or bromo; $R_6$ is hydrogen, halo wherein halo is fluoro, chloro, or bromo, methyl or methylene with the proviso that if there is a double bond between the 6 and 7 position $R_6$ is limited to hydrogen, methyl, or halo; $R_7$ is hydrogen or methyl; $R_9$ is α-hydrogen or α-fluoro; Rphd 11 is hydrogen, OX or keto or $R_9$ and $R_{11}$ taken together are a β-epoxide or a double bond; $R_{16}$ is hydrogen or methylene, methyl or OX; $R_{21}$ is H, halo or OX; wherein X is hydrogen, trimethylsilyl, or —CO—Y, wherein Y is lower alkyl or phenyl;

Formula B wherein $R_2$ through $R_{16}$ are as defined above; $R_{20}$ is hydrogen, methyl, allenyl or —C≡C—Z; wherein Z is hydrogen or alkyl of from one to five carbons, inclusive;

Formula C wherein $R_2$, $R_7$, $R_9$, $R_{11}$, $R_{16}$, and $R_{21}$ are as defined above; W is alkyl of from one to five carbons, inclusive, and $R_6'$ is hydrogen, methyl or halo; wherein halo is fluoro, chloro or bromo; or

Formula D wherein $R_2$, $R_6'$, $R_7$, $R_9$, $R_{11}$, $R_{16}$, $R_{20}$, and W are as defined above.

Most preferred among the compounds of formula II having a steroidal ring system denoted above as formula A for use within the novel processes of the present invention are:

17α-hydroxyprogesterone-3-enol methyl ether;
17α-hydroxy-6α-methyl-9β, 11β-oxido-pregna-1,4-dien-3,20-dione;
11β, 17α-dihydroxy-9α-fluoro-6α-methylpregna-1,4-dien-3,20-dione;
17α-hydroxy-6-methyl-16-methylenepregna-4,6-dien-3,20-dione;
21-acetoxy-6α-fluoro-17α-hydroxy-16β-methyl-9β, 11β-oxidopregna-1,4-dien-3,20-dione; and
17α,21-dihydroxy-6α-fluoro-16β-methyl-9β, 11β-oxidopregna-1,4-dien-3,20-dione.

It is to be understood that enol esters means various alkenyl, such as vinyl, isopropenyl, or butenyl, preferably isopropenyl acylates in which the acylate moiety includes from 2 to 6 carbons, inclusive, for example, acetyl, propionyl, butyryl, pentanoyl or hyexanoyl. Preparation of such acylates is well known, for example, from reactions of enolizable aldehydes or ketones with acid halides, acid anhydrides, or ketene in the presence of strong acid. Ketene is prepared by pyrolysis of acetone (Hagemeyer, Jr. et al., loc. cit.) or acetic anhydride (Fisher, et al., J. Org. Chem. 18, 1055–7 (1953)), and reacts with acetone in the presence of strong acid to form isopropenyl acetate, from which other enol acylates may be formed by acid-catalyzed exchange reactions with the appropriate carboxylic acid or enolizable carbonyl compound (Hagemeyer, Jr., et al., loc. cit.; Smith and Chen., J. Org. Chem. 30, 3095–3099 (1965)).

Preferably, isopropenyl acetate is used in the invention process.

Compounds of the formula II are generally known in the art. Particularly, examples of the most preferred steroids having the OH of formula II ROH, named above, attached to a steroidal ring system can be found in U.S. Pat. Nos. 2,867,638, 2,891,079, 3,000,914, 3,043,932, 3,061,616, 3,084,174, 3,105,840, 3,117,966, 3,147,290, 3,356,573, 3,400,137, and British Patent Nos. 868,303, 870,286, and 886,619.

The novel processes for producing the compounds of formula I according to the present invention are generally carried out by preparing a mixture of enol acylate, preferably isopropenyl acetate, and strong base in an aprotic solvent, such as toluene, dichloromethane, tetrahydrofuran, 1,2-dimethoxyethane, chlorobenzene, bis(2-methoxyethyl)ether, methyl acetate, pyridine or ethyl acetate and mixtures thereof, but preferably tetrahydrofuran, bis(2-methoxyethyl)-ether or dichloromethane. It is suggested the mixture include from 0.1 to 2 equivalents of strong base catalyst to compound of formula II, to be acylated; however, these ratios are not critical to the reaction.

The molar ratio of enol acylate to alcohol must be at least one. In some cases, it may be preferable to use enol acylate as the reaction solvent. The ratio of enol acylate to base is not critical except where competing reactions can occur, in which case higher ratios are preferred. The temperature of the mixture is maintained from −100° C. to reflux temperature, preferably −35° C. to +95° C., and most preferably from −20° C. to +30° C. throughout the reaction. The strong base which is used as the catalyst is selected from 4-dimethylaminopyridine, diazabicyclo[5.4.0]undec-7-ene(DBU), metal; such as aluminum, magnesium, titanium or monovalent metal; alkoxides or a metal salt of an enolizable alkyl compound, for example, which is prepared from NaH and acetone by known methods. The alkoxides are preferred and include, for example, methoxide, ethoxide, propoxide, isopropoxide, butoxide, isobutoxide, tert-butoxide or amyl- oxide or higher alkoxides, also including isomers of both latter groups. In general, sodium alkoxides are preferred when $C_{21}$ is a methyl group, while lithium alkoxides are preferred when $C_{21}$ is an acyloxymethyl group. Most preferred among the bases are monovalent metal; for example, lithium, potassium or sodium, alkoxides. The preferred order of assembling the reaction mixture may vary depending on the possibility of interactions between the compounds of the reaction within experimental skill of artisans. The product I is separated from the reaction mixture by conventional means, including distillation (may be advantageous under less than atmospheric pressure), scavenging the enol ester with, for example, methanol, extraction crystallization or combinations of these.

Many advantages attend the use of the processes of this invention such as obviating the necessity of protecting any acid-sensitive functional groups on R. Additionally, for example, a specific advantage is that little or no 3-enol acetate is formed by the novel process of the invention when used to acetylate the preferred hydroxy containing steroidal ring systems A and B in the formula noted above having a 3-ketone substituent. Likewise, the acid-sensitive epoxy group, for example, when $R_9$ and $R_{11}$ are taken together in the above noted compounds of formula A, B, C, and D is not destroyed when using the present processes.

The general reaction described above is applied to a wide range of alcohols having different degrees of activity. That is, similar reactions may be carried out with appropriate modifications depending on the starting materials and various combinations of reagents within the novel invention processes.

The following examples illustrate the novel aspects of this invention. However, these examples should not be considered limiting.

EXAMPLE I

17α-Acetoxyprogesterone-3-enol methyl ether

In a nitrogen filled dry box a 500 ml jacketed flask is purged with nitrogen, supplied with a magnetic stirring bar, thermometer and powder funnel, and connected to a circulating cooler. Redistilled isopropenyl acetate (80 ml, 72.7 g, 726 mmoles) is put in the flask and cooled to −14° C. Dry sodium methoxide (3.96 g, 73.3 mmoles) is then added, followed by dichloromethane (146 ml). After the resulting thin slurry is again at −14° (17α-hydroxyprogesterone-3-enol methyl ether (50.00 g, 145.1 mmoles) is added. The reaction temperature is then raised to 0° C.±2° C. for ~14.5 hours, at which time a few percent of starting material apparently remains.

Excess isopropenyl acetate is solvolyzed at −5° to 0° C. with methanol (20.46 g, 25.9 ml, 10% excess) containing 1% triethylamine. The heat of reaction is removed partly by the cooler and partly by distillation of dichloromethane and other low-boilers under vacuum. The addition is followed by similar addition during ~5 minutes of a solution of acetic acid (4.2 ml, 73.3 mmoles) and triethylamine (10.2 ml, 73 mmoles) in methanol (20 ml). Following another half hour of solvent removal under vacuum at −5° to 6° C., the reaction mixture may be held at −21° C. overnight. Samples before and after the holding period are indistinguishable by TLC.

Distillation under vacuum at −18° is resumed and continued, with a methanol −1% triethylamine mixture added as needed, until the distillate is essentially free of dichloromethane by NMR and the slurry volume is ~150 ml. The slurry is filtered and the cake washed with a methanol −1% triethylamine mixture (30 ml, then 10 ml). The cake is reslurried on the filter with a methanol −1% triethylamine mixture (60 ml), filtered, rinsed with the same solvent (15 ml), and dried on the filter (vacuum below the frit and nitrogen flowing through the cake) to give 52.76 g (94.0%) of white, crystalline 17α-acetoxyprogesterone-3-enol methylether.

M.P. 176°–183° C., $^1$H NMR (CDCl$_3$) δ 5.20 (m, 2H, C=CH—), 3.57 (s, 3H, —OCH$_3$), 2.10 (s, 3H, CH$_3$), 2.03 (s, 3H, CH$_3$), 0.97 (s, 3H, CH$_3$), 0.67 (s, 3H, CH$_3$).

EXAMPLE II

17α-Acetoxy-6α-methyl-9β,11β-oxidopregna-1,4-dien-3,20-dione

35 Grams of 17α-hydroxy-6α-methyl-9β,11β-oxidopregna-1,4-dien-3,20-dione (98 millimoles) in 140 ml dichloromethane is filtered. Excess dichloromethane is added and evaporated under vacuum to approximately 140 ml volume to remove any condensed water as the dichloromethane-water azeotrope. 54.1 Milliliters (490 millimoles, i.e. ratio of 5:1 of isopropenyl acetate to steroid) of isopropenyl acetate is added, causing a 2° exotherm. 4.15 Grams (76.9 millimoles) of sodium methoxide is added causing a 2.4° exotherm. The reaction proceeds rapidly between 1 and 1¾ hours. After 3 hours, when no starting material is shown by TLC, the reaction is quenched with 4 ml of acetic acid at 18° C. The reaction mixture, which remains amber brown during the reaction, decolorizes to yellow on quenching. 30 Milliliters of methanol is added to help quench the sodium methoxide. pH is <7 (reddish edges on pH paper). The solvent is vacuum distilled to 180 ml volume. Distilling is continued while 250 ml of methanol is added to replace the distillate. Then 50 ml methanol is added, dissolving the sodium acetate. 165 Milliliters of methanol is added and 17α-acetoxy-6α-methyl-9β,11β-oxidopregna-1,4-dien-3,20-dione is crystallized out. The mixture is cooled in an ice bath for ½ hour, filtered, and product slurried with cold methanol. Light yellow crystals of 17α-acetoxy-6α-methyl-9β,11β-oxidopregna-1,4-dien-3,20-dione result. The yield is 31.0527 g or 88.7% by weight. The product is 17α-acetoxy-6α-methyl-9β,11β-oxidopregna-1,4-dien-3,20-dione.

M.P. 217°–22° C., $^1$H NMR (CDCl$_3$) δ6.6 (d, 1H, J=10.5 Hz, —CH=), 6.25 (d. of d., 1H, J=10.5 Hz, J$_2$=2Hz, =CH—), 6.2 (s, 1H, =CH—), 3.4 (s, 1H, CH—), 2.10 (s, 3H, —OCH$_3$), 2.04 (s, 3H, CH$_3$—), 1.45 (s, 3H, CH$_3$—), 1.20 (d, 3H, J=6Hz, CH$_3$), 0.85 (s, 3H, CH$_3$—).

When the starting material, 17α-hydroxy-6α-methyl-9β,11β-oxidopregna-1,4-diene-3,20-dione is purified, this reaction also performs well at 50 fold scale up.

EXAMPLE III

17α-Acetoxy-6-methyl-16-methylenepregna-4,6-dien-3,20-dione

A mixture of sodium methoxide (14.4 mmoles), tetrahydrofuran (30 ml), isopropenyl acetate (84.4mmoles), and 17α-hydroxy-6-methyl-16-methylenepregna-4,6-dien-3,20-dione (28.2 mmoles) is prepared at −16° C. and kept at −16° to −21° C. during 20.3 hours. Excess isopropenyl acetate is solvolyzed >−9° C. with methanol (104 mmoles), and sodium methoxide is neutralized with acetic acid (114.3 mmoles) at −20°. Methyl acetate, acetone, methanol and tetrahydrofuran were distilled under vacuum at ≦18° C. while being replaced by 2-propanol. When NMR showed the distillate to be free of tetrahydrofuran, the resulting thick slurry was stirred at ambient temperature for one hour, then filtered. The filter cake was washed with 2-propanol (2×10 ml.), water (10 ml., to remove sodium acetate), and 2-propanol (5 ml.). Drying under reduced pressure at ambient temperature gave 23.5 mmoles of the 17α-acetate, m.p. 218°–221° C., $^1$H NMR (CDCl$_3$) δ5.90 (d, 2H, C=CH—), 5.52 (d, 2H, J=2Hz, C=CH$_2$), 2.13 (s, 3H, CH$_3$), 2.03 (s, 3H, CH$_3$), 1.85 (s, 3H, CH$_3$), 1.10 (s, 3H, CH$_3$), 0.77 (s, 3H, CH$_3$).

EXAMPLE IV

17α,21-Diacetoxy-6α-fluoro-16β-methyl-9β,11β-oxidopregna-1,4-dien-3,20-dione 1.06 Grams (2.45 millimoles) of 17α,21-dihydroxy-6α-fluoro-16β-methyl-9β,11β-oxidopregna-1,4-dien-3,20-dione, 21-acetate is mixed with 3.5 ml of tetrahydrofuran (THF). 1.35 Milliliters of isopropenyl acetate is added and the mixture is cooled to 6.5° C. 61.3 Milligrams (1.1 millimoles) of lithium ethoxide is added causing an exotherm of about 13° C., controlled with an ice bath. After ½ hour the mixture is dark orange. In 40 minutes a precipitate forms. After 1.5 hours TLC shows the reaction is essentially complete. It is then quenched with 0.07 ml of acetic acid and is stirred at room temperature overnight. The mixture turns to a light yellow. The mixture is dissolved in dichloromethane, methanol is added and the mixture is concentrated to near dryness. The residue is redissolved in 6 ml of dichloromethane and 3 ml of methanol, then the solution is evaporated to 4 ml. Upon cooling to 0° C., yellow granular crystals (1.07 g, 91.8%) of 17α,21-diacetoxy-6α-fluoro-16β-methyl-9β,11β-oxidopregna-1,4-dien-3,20-dione are obtained.

M.P. 219°-9.5° C., 'H NMR (CDCl₃) δ6.60 (d, 1H, J=10Hz, —CH=), 6.45 (s, 1H, —CH=) 6.30 (d of d, 1H, J, =10Hz, J₂=2Hz, =CH—), 5.45 (d of q, 1H, J, =51Hz, —CHF—), 4.60 (d of d, 2H, J=17.3 Hz, —CH₂OAc), 3.40 (s, 1H,

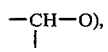

2.20 (s, 3H, —OCH₃), 2.19 (s, 3H, CH₃), 1.50 (s, 3H, —CH₃), 1.35 (d, 3H, J=6Hz, CH₃—), 0.90 (s, 3H, CH₃—).

EXAMPLE V

17α,21-Diacetoxy-6α-fluoro-16β-methyl-9β,11β-oxidopregna-1,4-dien-3,20-dione 2.45 Millimoles (957 milligrams) of 17α,21-dihydroxy-6α-fluoro-16β-methyl-9β, 11β-oxidopregna-1,4-dien-3,20-dione is added to 3.5 ml of tetrahydrofuran (THF). 2.02 Milliliters (18.4 millimoles or a ratio of 7.5:1 isopropenyl acetate to steroid) of isopropenyl acetate is added. At room temprature, 63.4 mg (1.22 millimoles, a ratio of 0.5:1 lithium ethoxide to steroid) of lithium ethoxide is added. There is no change initially. The reaction is slowly exothermic (2 minutes to 6 minutes causes a temperature rise of 5.5° C.) and slowly turns yellower. At 10 minutes the color of the reaction is dark yellow to brown and the temperature is decreasing. TLC shows the reaction is almost complete within 10 minutes. Very slowly during 45 minutes the reaction mixture becomes dark and mostly a solution. After 2.5 hours some 21-acetoxy-6α-fluoro-17α-hydroxy-16β-methyl-9β,11β-oxidopregna-1,4-dien-3,20-dione remains, therefore, 12 milligrams of lithium ethoxide is added so that the total lithium ethoxide used is 1.45 millimoles or a ratio of 0.6:1 lithium ethoxide to steroid. No visible changes are seen. After an additional 25 minutes, TLC shows little 17α,21-dihydroxy starting material or 21-acetoxy-17α-hydroxy intermediate. The reaction mixture is quenched at 3.75 hours with 0.09 ml of acetic acid (10% excess, 1.575 millimoles). It is stirred at room temperature overnight. The TLC now looks the same as before the quenching. The mixture is diluted with dichloromethane and methanol to dissolve the precipitate, then the solution is evaporated almost to dryness and the residue redissolved in 5 ml of dichloromethane and 4 ml of methanol. It is again evaporated to a volume of about 3 or 4 ml. Orange crystals of 17α,21-diacetoxy-6α-fluoro-16β-methyl-9β,11β-oxidopregna-1,4-dien-3,20-dione are produced. The yield is 0.83 g (71.7% of theory). The NMR of these crystals is consistent with the NMR of the desired product (see Example V).

FORMULAE

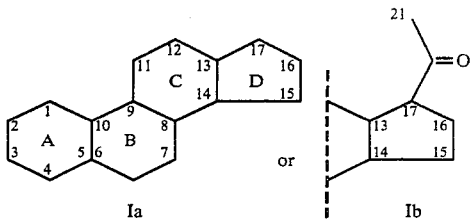

Ia or Ib

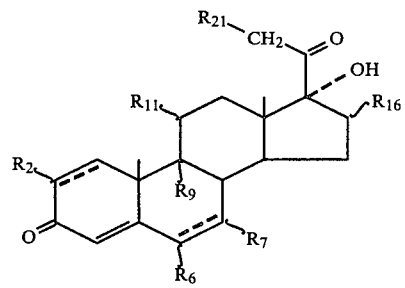

A

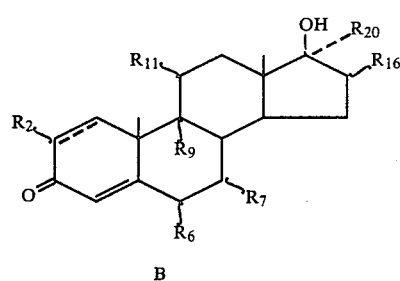

B

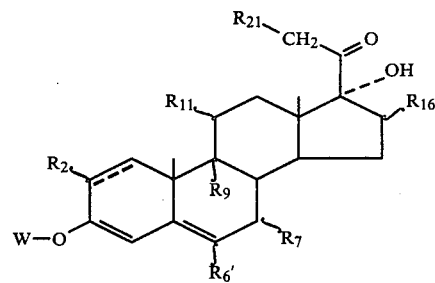

C

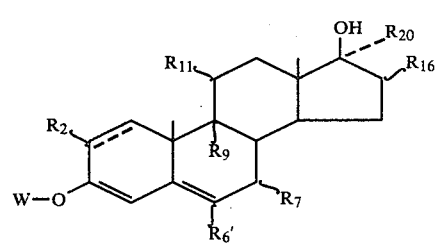

D

We claim:
1. In a process comprising acylating an alcohol wherein the improvement comprises reacting the alcohol with an enol ester using a strong base as catalyst.
2. A process according to claim 1 wherein the alcohol is selected from the group consisting of a tertiary alco- hol, hindered alcohol or alcohol additionally having an acid sensitive functionality present.

3. A process for the preparation of a compound having the formula

ROAc       I in which R is alkyl, alkenyl, aryl, aralkyl, cycloalkyl, alkyl substituted cycloalkyl, cycloalkenyl, heterocyclic ring or steroidal ring system, and Ac is an acyl group of from 2 to 6 carbons, inclusive, which comprises reacting an enol ester with an alcohol having the formula

ROH       II wherein R is as defined above, in the presence of a strong base as catalyst.

4. A process according to claim 3 wherein the alcohol includes a steroidal ring system such that the alcohol is selected from the formulae

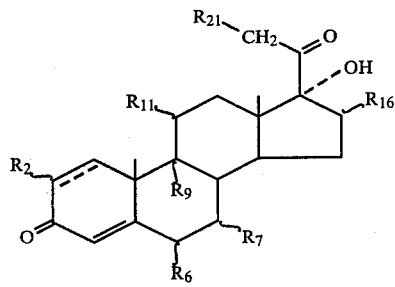

A

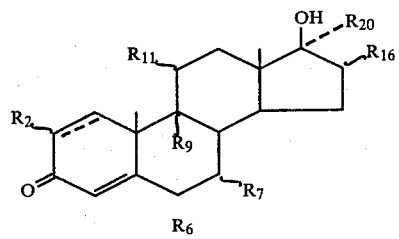

B

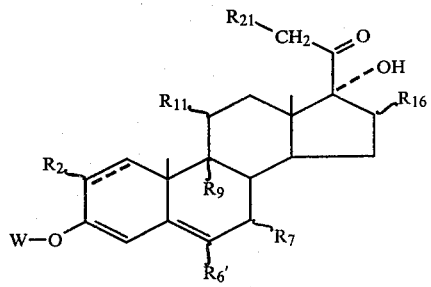

C

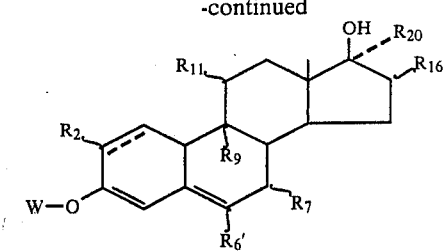

D wherein ~ is α or β; ═ is an optional double bond; $R_2$ is hydrogen or halo wherein halo is fluoro, chloro, or bromo; $R_6$ is hydrogen, halo; wherein halo is fluoro, chloro, or bromo, methyl or methylene with the proviso that if there is a double bond between the 6 and 7 position $R_6$ is limited to hydrogen, methyl, or halo; W is alkyl of from one to 5 carbons, inclusive, and $R_6'$ is hydrogen, methyl or halo; wherein halo is fluoro, chloro or bromo; $R_7$ is hydrogen or methyl; $R_9$ is hydrogen or fluoro; $R_{11}$ is hydrogen, OX or keto or $R_9$ and $R_{11}$ taken together are a β-epoxide or a double bond; $R_{16}$ is hydrogen or methylene, methyl or OX; $R_{20}$ is hydrogen, methyl, allenyl or —C≡C—Z wherein Z is hydrogen or alkyl of from one to 5 carbon atoms, inclusive; $R_{21}$ is H, halo or OX; wherein X is hydrogen, trimethylsilyl, or —CO—Y, wherein Y is lower alkyl or phenyl.

5. A process according to claim 4 wherein the alcohol is 17α-hydroxyprogesterone-3-enol methyl ether.

6. A process according to claim 4 wherein the alcohol is 17α-hydroxy-6-α-methyl-9β,11β-oxido-pregna-1,4-diene-3,20-dione.

7. A process according to claim 4 wherein the alcohol is 11β,17α-dihydroxy-9α-fluoro-6α-methylpregna-1,4-dien-3,20-dione.

8. A process according to claim 4 wherein the alcohol is 17α-hydroxy-6-methyl-16-methylenepregna-4,6-dien-3,20-dione.

9. A process according to claim 4 wherein the alcohol is 21-acetoxy-6α-fluoro-17α-hydroxy-16β-methyl-9β,11β-oxidopregna-1,4-dien-3,20-dione.

10. A process according to claim 4 wherein the alcohol is 17α,21-dihydroxy-6α-fluoro-16β-methyl-9β,11β-oxidopregna-1,4-dien-3,20-dione.

11. A process according to claims 1, 3, 4, 5, 6, 7, 8, 9 or 10 wherein the enol acylate is isopropenyl acetate.

12. A process according to claim 11 wherein the strong base is 4-dimethylaminopyridine, diazabicyclo[5.4.4]-undec-7-ene, a metal alkoxide or a metal salt of an enolizable carbonyl compound prepared from NaH and acetone.

13. A process according to claim 12 wherein the metal salt is a compound prepared from NaH and acetone.

14. A process according to claim 12 wherein the strong base is a monovalent metal alkoxide.

15. A process according to claim 14 wherein the alcohol is 17α-hydroxyprogesterone-3-enol methyl ether and the strong base is sodium methoxide.

16. A process according to claim 14 wherein the alcohol is 21-acetoxy-6α-fluoro-17α-hydroxy-16β-methyl-9β,11β-oxidopregna-1,4-dien-3,20-dione or 17α,21-dihydroxy-6α-fluoro-16β-methyl-9β,11β-oxidopregna-1,4-dien-3,20-dione and the strong base is lithium ethoxide.

* * * * *

UNITED STATES PATENT OFFICE
CERTIFICATE OF CORRECTION

Patent No. 4,346,037          Dated August 24, 1982

Inventor(s) Howard J. Burke et al

It is certified that error appears in the above-identified patent and that said Letters Patent are hereby corrected as shown below:

Col. 3, line 3: "is α or β;     is an" should read: --is α or β; ----- is an--.

Col. 3, line 10: "Rphd 11 is hydrogen" should read: --$R_{11}$ is hydrogen--.

Col. 6, line 34: "solvolyzed >-9° C. with" should read: --solvolyzed <-9° C with--.

Col. 6, line 38: "at ≦18° C. while" should read: --at ≦18° while--.

Col. 8, Formula B should appear as follows instead of as in the patent:

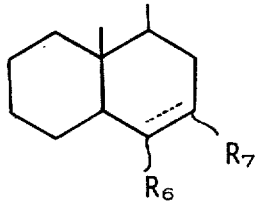

Col. 9, Formula A should appear as follows instead of as in the patent:

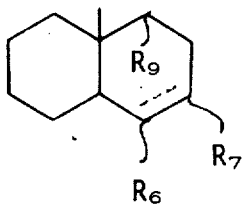

UNITED STATES PATENT OFFICE
CERTIFICATE OF CORRECTION

Patent No. 4,346,037　　　　　　Dated August 24, 1982

Inventor(s) Howard J. Burke et al

It is certified that error appears in the above-identified patent and that said Letters Patent are hereby corrected as shown below:

Col. 9, Formula B should appear as follows instead of as in the patent:

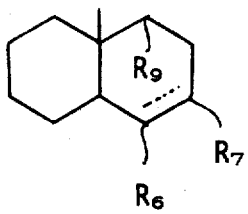

Signed and Sealed this

Second Day of August 1983

|SEAL|

Attest:

Attesting Officer

GERALD J. MOSSINGHOFF

Commissioner of Patents and Trademarks